United States Patent [19]

Laugier et al.

[11] Patent Number: 5,358,716
[45] Date of Patent: Oct. 25, 1994

[54] PHARMACEUTICAL COMPOSITION FOR TOPICAL APPLICATION CONTAINING DITHRANOL AND PREPARATION PROCESS

[75] Inventors: Jean-Pierre Laugier, Antony; Evelyne Segot, Nogent-sur-Marne, both of France

[73] Assignee: L'Oreal, Paris, France

[21] Appl. No.: 945,703

[22] Filed: Sep. 16, 1992

[30] Foreign Application Priority Data

Sep. 17, 1991 [FR] France .................. 91 11417

[51] Int. Cl.$^5$ ............... A61K 9/127; A61K 31/05
[52] U.S. Cl. ........................... 424/450; 514/863; 514/772.6
[58] Field of Search ............ 424/450, 78.03, 78.06, 424/78.07, 78.38; 514/772.3, 772.6, 863

[56] References Cited

U.S. PATENT DOCUMENTS

| | | | |
|---|---|---|---|
| 4,438,052 | 3/1984 | Weder et al. | 424/450 |
| 4,731,210 | 5/1988 | Weder et al. | 436/829 |
| 4,954,345 | 9/1990 | Muller | 424/450 |
| 5,055,228 | 10/1991 | Zabotto et al. | 252/312 |

FOREIGN PATENT DOCUMENTS 0234328  3/1990  European Pat. Off. .

OTHER PUBLICATIONS

Chem. Ab. 115:287091b.

Primary Examiner—Thurman K. Page
Assistant Examiner—Peter F. Kulkosky
Attorney, Agent, or Firm—Cushman, Darby & Cushman

[57] ABSTRACT

Pharmaceutical composition for topical application to the skin, comprising an oil-in-water emulsion containing dithranol. This composition contains, in order to prevent the oxidation of the dithranol, nonionic vesicles prepared from a lipid phase containing at least one nonionic amphiphilic lipid. These vesicles are dispersed in the aqueous phase of the emulsion.

14 Claims, No Drawings

PHARMACEUTICAL COMPOSITION FOR TOPICAL APPLICATION CONTAINING DITHRANOL AND PREPARATION PROCESS

The present invention relates to a pharmaceutical composition for topical application containing dithranol and a process for preparing said composition.

Dithranol is a compound of formula $C_{14}H_{10}O_3$, also known by the name anthralin, 1,8,9-trihydroxyanthracene or 1,8-dihydroxyanthranol.

Pharmaceutical compositions containing dithranol are commonly used in the treatment of psoriasis by topical application onto the skin. However, the use of dithranol has numerous disadvantages because it has a strong irritative action on the skin and is unstable in oxygen and other compounds such as water and alkaline bases. A 1,8-dihydroxyanthraquinone, which itself leads to other compounds called "brown anthralin" which are brown in colour and which indelibly stain clothing, is formed from dithranol by oxidation.

To avoid the problems due to the instability of dithranol, it has been proposed to prepare anhydrous compositions because in these compositions, the chemical stability of dithranol poses relatively fewer problems than in an aqueous medium. However, these compositions have the disadvantage of not being easily removable with water; the contact time between the and the composition is therefore difficult to control and, consequently, the skin may be irritated.

It is known that compositions in which dithranol is dispersed in an oil-in-water or water-in-oil type emulsion can be removed by washing with water. These compositions therefore make it possible to control the contact time between dithranol and the skin and, consequently, to carry out treatment of the psoriasis-affected areas by the so-called "Short Contact Therapy" process.

However it is necessary to add an antioxidant to these aqueous phase-containing compositions in order to avoid the oxidation of dithranol, the consequence cf which oxidation is to impart a chestnut colour to the composition.

Yet it is well known that antioxidants are capable of causing dermatitis or allergic reactions of the skin (see for example CONTACT DERMATITIS 1987 Vol 17 p. 294–298; 1984 Vol 11, p. 265–267; 1987, Vol 16 p. 260–262 and 1988 Vol 5 p. 313–314, MARTINDALE 29th Ed. p. 1361 and 1362; JAAD Vol 13 N6 December 1985 p. 1062–1069 (R. ADAMS and H. RAIBACH); JID 85: 351–356, 1985 (DENEZZA et al) and DE-A 3,540,175).

Consequently, efforts are being made to obtain a composition in which dithranol is stable in the aqueous phase without the need for an antioxidant to be added.

In DE-A 3,540,175, it has been proposed to stabilise compositions containing dithranol by adding a self-emulsifying additive which may be a fatty acid glyceride ester, a lactyllactic acid fatty acid ester, a polyglycerolated fatty acid ester or 2-hydroxyalkylated esters. Compositions were prepared according to Examples 2 and 3 of this application and were left in contact with air. After a few hours, the formation of a brown coloration due to the oxidation o#dithranol was observed.

It is also known from DE-A 3,542,773 that the penetration rate of active ingredients, in particular dithranol, is improved by encapsulating these active ingredients in liposomes prepared from ionic amphiphilic lipids such as phospholipids. However, it should be noted that, as shown in the comparative examples given below, the encapsulation of dithranol in liposomes does not prevent its oxidation.

According to the present invention, it has been found unexpectedly that the oxidation of dithranol is prevented by adding vesicles containing a nonionic amphiphilic lipid to an oil-in-water type emulsion containing dithranol.

The subject of the present invention is therefore a pharmaceutical composition for topical application comprising an oil-in-water type emulsion containing dithranol, characterised in that the emulsion contains, in dispersed form, vesicles prepared from a lipid phase containing at least one nonionic amphiphilic lipid.

Indeed, it has been found that in the presence of lipid phase-vesicles containing a nonionic amphiphilic lipid or niosome, the dithranol present in an oil-in-water emulsion does not become oxidised. The dithranol is therefore stable and the dithranol content of the compositions does not decrease during storage. Furthermore, the compositions containing nonionic vesicles or niosomes do not become coloured or only acquire a faint chestnut colour when they are in contact with air. There is therefore no risk of the user's clothing becoming indelibly stained.

Moreover, it should be noted that in a known manner, as described in FR-A 2,490,504, the nonionic vesicles stabilise the oil-in-water emulsion containing the dithranol. It is not therefore necessary to add an emulsifying agent.

The composition according to the invention therefore consists of an aqueous phase in which the oil droplets of the oil-in-water emulsion and the nonionic vesicles are dispersed. The dithranol is present in the solubilised or dispersed form in the oil or in the aqueous phase. It should be noted that it is not. encapsulated in the nonionic vesicles.

The nonionic amphiphilic lipids present in the lipid phase are preferably those having the formula:

formula in which:

—$C_3H_5(OH)$—O— is represented by the following structures taken together or separately:

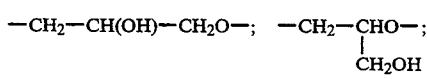

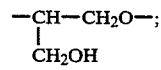

$\overline{n}$ is a mean statistical value between 2 and 6;

$R_1$ represents a residue of formula:

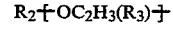

where:

$R_2$ represents a linear or branched, saturated or unsaturated alkyl radical containing 12 to 18 carbon atoms or, alternatively, a $R_4CO$ residue where $R_4$ is a linear or branched $C_{11}$–$C_{17}$ aliphatic radical;

$OC_2H_3(R_3)$— is represented by the following structures taken together or separately:

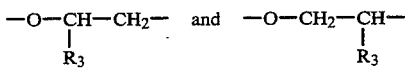

where $R_3$ has the meaning given for $R_2$.

In a known manner, at least one additive intended to improve the physicochemical stability and the permeability of the vesicles to the encapsulated substances can be combined, in the lipid phase, with the nonionic amphiphilic lipid(s). Among the known additives, there may be mentioned long chain alcohols and diols; sterols, more particularly cholesterol and beta-sitosterol; long chain amines and their quaternary ammonium derivatives, for example dodecyldimethylammonium bromide or bishydroxyalkylamines; polyoxyethylenated fatty amines or their salts; long chain aminoalcohol esters as well as their salts and quaternary ammonium derivatives; alkyl sulphates, for example sodium cetyl sulphate; and ionic derivatives of sterols such as cholesterol phosphate and sulphate. Within the scope of the present invention, the fatty alcohol phosphoric esters, for example sodium dicetyl or dimyristyl phosphate, are particularly appropriate; these phosphoric esters may also be advantageously combined with cholesterol.

The nonionic vesicles or niosomes may, in a known manner, encapsulate hydrophilic and/or lipophilic substances having a cosmetic or dermopharmaceutical activity.

The lipid phase in the form of nonionic vesicles represents between 2% and 14% by weight of the composition.

The pharmaceutical composition contains 0.05 to 5% by weight of dithranol relative to the composition, preferably 0.2 to 2% by weight, the dithranol is introduced in the form of a powder, preferably micronised when its concentration is greater than 0.15% by weight.

The oily phase of the oil-in-water type emulsion generally consists of a saturated oil which is liquid at room temperature. This oil may be an oil of vegetable or animal origin which is taken from the group made up of esters of fatty acids and polyols, such as glycerol tricaprocaprylate and esters of a fatty acid and branched alcohols, of formula $R_5COOR_6$ in which $R_5$ represents the residue of a $C_8$–$C_{20}$ higher fatty acid and $R_6$ represents a $C_3$–$C_{20}$ hydrocarbon chain, such as isopropyl myristate.

The oil may also be a hydrocarbon or a polysiloxane. The hydrocarbon is for example vaseline, paraffin oil or perhydrosqualene. The polysiloxane is for example cyclomethicone, dimethylpolysiloxane or phenylpolysiloxane.

The amount of oil present in the composition is between 5 and 30% by weight of the composition, preferably between 15 and 25%.

In a known manner, fat-soluble cosmetic or dermopharmaceutical additives may be introduced into the oily phase.

The aqueous phase of the emulsion may also contain water-soluble cosmetic or dermopharmaceutical active ingredients.

According to the present invention, the aqueous phase is preferably gelled. Among the gelling agents which can be used, cellulose derivatives, algae derivatives or natural gums may be mentioned. The use of hydroxyethyl cellulose or polycarboxyvinylic acid such as for example "CARBOPOL 940" sold by the company GOODRICH, is preferred.

The gelling agent is generally added in amounts of between 0.1 and 2% by weight relative to the composition.

In a known manner, pharmaceutically acceptable additives having no pharmaceutical activity and which are generally used in the formulation of compositions for topical application, may also be introduced into the composition according to the invention. These pharmaceutically acceptable additives are preferably taken from the group made up of bactericides, preservatives, chelating agents, opacifiers or colorants; in particular, antibacterial preservatives such as methyl para-hydroxybenzoate and propyl para-hydroxybenzoate are added.

The composition is preferably prepared in the following manner:

vesicles in the form of a dispersion in an aqueous phase are prepared by any known process from a lipid phase;

in addition, a dispersion of powdered dithranol in the oily phase is prepared separately;

optionally, a gel is also prepared separately from a gelling agent in an aqueous phase;

the dispersion of dithranol into the oily phase is incorporated, in a homogeniser, into the dispersion of vesicles in an aqueous phase;

and finally, the gel is optionally added.

Preferably, the dispersion of vesicles in an aqueous phase is prepared by melting the lipid phase, hydrating the melted lipid phase, with stirring, in order to obtain a lamellar phase followed by the addition of additional amount of aqueous phase and homogenisation in order to obtain vesicles in the form of a dispersion in an aqueous phase.

The examples given below are given in order to illustrate the invention without limiting it.

EXAMPLE 1

Comparative 3 compositions containing dithranol in an oil-in-water type emulsion were prepared for comparative purposes.

A) Composition A according to the invention having the following formulation (in % by weight):

| | |
|---|---|
| Lipid phase | 8% |
| consisting of: | |
| Nonionic amphiphilic lipid consisting of diglycerol hexadecyl ether of formula II | 3.8% |
| $C_{16}H_{33}O(CH_2-\underset{\underset{OH}{\|}}{CH}-CH_2O)_2H$ | |
| Dicetyl phosphate | 0.4% |
| Cholesterol | 3.8% |
| Caprylic and capric acid triglyceride sold under the trade name "MIGLYOL 812" by the company DYNAMIT NOBEL | 15% |
| Dithranol | 0.3% |
| Polycarboxyvinylic acid sold under the trade name "CARBOPOL 940" by the company GOODRICH | 0.6% |
| Triethanolamine qs pH | 3.6% |
| Purified water qs | 100.0% |

Composition A is prepared in the following manner. The melting of the lipid phase is performed at 110° C. and then the melted lipid phase is hydrated using 22% of water by weight relative to the total composition, at 80° C., in order to obtain a lamellar phase; the hydration is continued by adding 30% water by weight relative to the total composition, at 70° C., and the mixture is transferred to a high pressure homogeniser in order to obtain vesicles dispersed water.

In addition, a suspension of dithranol oil, consisting of "MIGLYOL 812", is prepared by of a turbine.

A "CARBOPOL 940" gel, neutralised with triethanolamine, is prepared separately.

Finally, the suspension of dithranol is incorporated into the dispersion of vesicles in water by means of a high pressure homogeniser and then the neutralised "CARBOPOL 940" gel is incorporated.

B) Composition B (not forming part of the invention) containing dithranol in an oil-in-water type emulsion with an anionic surfactant.

| -continued | |
|---|---|
| Dithranol | 0.30% |
| "CARBOPOL 940" | 0.60% |
| Triethanolamine qs pH | 3.6 |
| Purified water qs | 100.0% |

This composition D is prepared using a process similar to that for the composition A.

100 g of compositions A to D were left in contact with air at various temperatures, for 1 and 2 months and then the amount of dithranol remaining in the composition after exposure to air was assayed in grams and the percentage degradation was calculated.

The results are given in Table I below.

| COMPOSITION | A | | B (1) | | C (1) | | D (1) | |
|---|---|---|---|---|---|---|---|---|
| | Weight of dithranol in g | % degradation | Weight of dithranol in g | % degradation | Weight of dithranol in g | % degradation | Weight of dithranol in g | % degradation |
| Time 0 | 0.276 | — | 0.303 | — | 0.263 | — | 0.239 | — |
| 1 month RT (2) | 0.273 | 1.08 | 0.259 | 14 | 0.255 | 3 | 0.229 | 4 |
| 2 months RT | 0.278 | NS (3) | 0.248 | 18 | 0.243 | 7.6 | 0.255 | 6 |
| 1 month 37° C. | 0.273 | 1.08 | 0.251 | 17 | 0.248 | 5.7 | 0.227 | 7 |
| 2 months 37° C. | 0.274 | NS (3) | 0.220 | 27 | 0.220 | 16 | 0.216 | 9.6 |
| 1 month 45° C. | 0.274 | NS (3) | 0.237 | 21.7 | 0.212 | 19 | 0.221 | 7.5 |
| 2 months 45° C. | 0.274 | NS | 0.111 | 63 | 0.118 | 55 | 0.121 | 49 |

(1) Does not form part of the invention
(2) RT: Room temperature
(3) NS: Not significant The composition is of the following (in % by weight):

| Sodium lauryl sulphate | 8% |
|---|---|
| "MIGLYOL 812" | 15% |
| Dithranol | 0.30% |
| "CARBOPOL 940" | 0.60% |
| Triethanolamine qs pH | 3.6 |
| Water qs | 100.0% |

C) Composition C (not forming part of the invention) containing dithranol in an oil-in-water emulsion with a nonionic surfactant.

The composition is of the following formula:

| Nonionic surfactant consisting of: | 8% |
|---|---|
| a mixture of glyceryl stearate and polyethylene glycol stearate 100 sold under the trade name "ARLACEL 165" by the company ICI | 6% |
| a polysorbate sold under the trade name "TWEEN 60" by the company ICI | 2% |
| "MIGLYOL 812" | 15% |
| Dithranol | 0.30% |
| "CARBOPOL 940" | 0.60% |
| Triethanolamine qs pH | 3.6% |
| Purified water qs | 100.0% |

D) Composition (not forming part of the invention) containing vesicles of an ionic amphiphilic lipid.

| Lipid phase consisting of soybean lecithin sold under the trade name "EPIKURON 145 V" by the company LUCAS MEYER | 8% |
|---|---|
| "MIGLYOL 812" | 15% |

Table I shows that dithranol is only stable in the composition A according to the invention. In the other compositions (B, C, D), it would be necessary to add an antioxidant in order to stabilise the dithranol.

EXAMPLE 2

Cream Containing 2.5% of Dithranol

A cream having the following formula was prepared using a process similar to that described for composition A:

nonionic amphiphilic lipid of formula:

$$R_4-O$$
$$|$$
$$CH_2$$
$$|$$
$$R_5-CH-O-(CH_2-CH-O)_{\overline{n}}H$$
$$|$$
$$CH_2OH$$

n = 6
$R_4 = C_{12}H_{25}$
$R_5 = C_{14}H_{29}/C_{16}H_{33}$

| | |
|---|---|
| | 10.0 g |
| Ditetradecyl phosphate | 1.0 g |
| Perhydrosqualene | 25.0 g |
| Micronised dithranol | 2.5 g |
| Polycarboxyvinylic acid sold under the trade name "CARBOPOL 940" by the company GOODRICH | 0.6 g |
| Methyl para-hydroxybenzoate | 0.1 g |
| Propyl para-hydroxybenzoate | 0.05 g |
| 10% Sodium hydroxide qs pH | 3.6 |
| Purified water qs | 100.0 g |

It was verified that the cream had not acquired a brown coloration after 48 hours of exposure to air at room temperature.

EXAMPLE 3

Cream Containing 2% of Dithranol

A cream having the following formula is prepared:

| | |
|---|---|
| Nonionic amphiphilic lipid of Example 1 | 9.0 g |
| Ditetradecyl phosphate | 1.0 g |
| Vaseline oil | 25.0 g |
| Micronised dithranol | 2.0 g |
| Polycarboxyvinylic acid sold under the trade name "CARBOPOL 940" by the company GOODRICH | 0.75 g |
| Methyl para-hydroxybenzoate | 0.1 g |
| Propyl para-hydroxybenzoate | 0.05 g |
| Triethanolamine qs pH | 3.5 |
| Purified water qs | 100.0 g |

It was verified that the cream had not acquired a brown coloration after 48 hours of exposure to air at room temperature.

EXAMPLE 4

Cream Containing 2% of Dithranol

A cream having the following formula was prepared:

| | |
|---|---|
| Nonionic amphiphilic lipid of Example 1 | 9.0 g |
| Ditetradecyl phosphate | 1.0 g |
| Vaseline oil | 25.0 g |
| Micronised dithranol | 2.0 g |
| Polycarboxyvinylic acid sold under the trade name "CARBOPOL 940" by the company GOODRICH | 0.75 g |
| Methyl para-hydroxybenzoate | 0.1 g |
| Propyl para-hydroxybenzoate | 0.05 g |
| Triethanolamine qs pH | 3.5 |
| Purified water qs | 100.0 g |

It was verified that the cream had not acquired a brown coloration after 48 hours of exposure to air at room temperature.

EXAMPLE 5

Cream Containing 0.05% of Dithranol

A cream having the following formula was prepared:

| | |
|---|---|
| Nonionic amphiphilic lipid of formula: $R_6-O-(CH_2-CH(CH_2OH)-O)_{\overline{n}}H$ <br> n = 3 <br> $R_6 = C_{16}H_{33}$ | 3.8 g |
| Cholesterol | 3.8 g |
| Dihexadecyl phosphate | 0.4 g |
| Caprylic and capric acid triglyceride sold under the name "MIGLYOL 812" by the company DYNAMIT NOBEL | 15.0 g |
| Dithranol | 0.05 g |
| Polycarboxyvinylic acid sold under the trade name "CARBOPOL 940" by the company GOODRICH | 0.6 g |
| Methyl para-hydroxybenzoate | 0.1 g |
| Propyl para-hydroxybenzoate | 0.05 g |
| Triethanolamine qs pH | 3.4 |
| Purified water qs | 100.0 g |

It was verified that the cream had not acquired a brown coloration after 48 hours of exposure to air at room temperature.

We claim:

1. Pharmaceutical composition for topical application comprising an oil-in-water type emulsion containing dithranol, wherein the emulsion contains, in dispersed form, vesicles prepared from a lipid wherein said lipid phase represents between 2 and 14 percent of said composition phase containing at least one nonionic amphiphilic lipid, the dispersion vesicles preventing oxidation of said dithranol without the addition of an antioxidant, wherein said composition has improved degradation resistance in comparison with the same composition not containing nonionic amphiphilic lipid.

2. Composition according to claim 1, characterised in that the nonionic amphiphilic lipid(s) is(are) of formula:

$$R_1O-[C_3H_5(OH)O]_{\overline{n}}H$$

formula in which:

—$C_3H_5(OH)$—O— is represented by the following structures taken together or separately:

$$-CH_2-CH(OH)-CH_2O-; \quad -CH_2-CHO-; \\ \qquad\qquad\qquad\qquad\qquad\qquad\qquad\quad | \\ \qquad\qquad\qquad\qquad\qquad\qquad\qquad\quad CH_2OH$$

$$-CH-CH_2O-; \\ | \\ CH_2OH$$

$\overline{n}$ is a mean statistical value between 2 and 6;
$R_1$ represents a residue of formula:

$$R_2+OC_2H_3(R_3)+$$

where:
$R_2$ represents a linear or branched, saturated or unsaturated alkyl radical containing 12 to 18 carbon atoms or, alternatively, a $R_4CO$ residue where $R_4$ is a linear or branched $C_{11}$-$C_{17}$ aliphatic radical;
$OC_2H_3(R_3)$— is represented by the structures taken together or separately:

$$-O-CH-CH_2- \quad \text{and} \quad -O-CH_2-CH- \\ | \qquad\qquad\qquad\qquad\qquad\qquad\quad | \\ R_3 \qquad\qquad\qquad\qquad\qquad\qquad\quad R_3$$

where $R_3$ has the meaning given for $R_2$.

3. Composition according to claim 1, characterised in that at least one additive intended to improve the stability and permeability of the vesicles is combined, in the lipid phase, with the nonionic amphiphilic lipid(s).

4. Composition according to claim 1, characterised in that the nonionic vesicles encapsulate hydrophilic and/or lipophilic substances having a cosmetic or dermopharmaceutical activity.

5. Composition according to claim 1, characterised in that it contains 0.05 to 5% by weight of dithranol.

6. Composition according to claim 1, characterised in that it contains 0.2 to 2% by weight of dithranol.

7. Composition according to claim 1, characterised in that the oily phase of the oil-in-water emulsion is an oil of vegetable or animal origin, a hydrocarbon or a polysiloxane.

8. Compositions according to claim 1, characterised in that the oily phase contains an oil-soluble cosmetic or dermopharmaceutical active ingredient.

9. Composition according to claim 1, characterised in that the aqueous phase of the oil-in-water type emulsion contains a water-soluble cosmetic or dermopharmaceutical active ingredient.

10. Composition according to claim 1, characterised in that the aqueous phase of the oil-in-water emulsion is gelled by a gelling agent.

11. Composition according to claim 10, characterised in that the gelling agent is a polycarboxyvinylic acid.

12. Compositions according to claim 10, characterised in that the gelling agent represents 0.1 to 2% by weight of the composition.

13. Process for preparing the composition according to claim 1, characterised in that:
- vesicles in the form of a dispersion in an aqueous phase are prepared from a lipid phase;
- in addition, a dispersion of powdered dithranol in the oily phase is prepared separately;
- the dispersion of dithranol in the oily phase is incorporated, in a homogeniser, into the dispersion of nonionic vesicles in an aqueous phase.

14. Process according to claim 13, characterised in that a gel is prepared separately from a gelling agent in an aqueous phase and it is added to the composition after incorporating the dispersion of dithranol into the dispersion of vesicles.

* * * * *